(12) United States Patent
Hahn

(10) Patent No.: US 6,217,326 B1
(45) Date of Patent: Apr. 17, 2001

(54) MOLD FOR PRODUCING A MODEL OF A TOOTH

(76) Inventor: Rainer Hahn, Schwabstrasse 11, D-72074 Tübingen (DE)

( * ) Notice: Subject to any disclaimer, the term of this patent is extended or adjusted under 35 U.S.C. 154(b) by 0 days.

(21) Appl. No.: 09/424,693

(22) PCT Filed: May 2, 1998

(86) PCT No.: PCT/EP98/02601

§ 371 Date: Mar. 6, 2000

§ 102(e) Date: Mar. 6, 2000

(87) PCT Pub. No.: WO98/52491

PCT Pub. Date: Nov. 26, 1998

(30) Foreign Application Priority Data

May 25, 1997 (DE) .............................................. 197 22 989

(51) Int. Cl.⁷ .................................................. A61C 9/00
(52) U.S. Cl. .................................................. 433/74; 433/36
(58) Field of Search ...................... 433/34, 60, 74, 433/37, 54, 213

(56) References Cited

U.S. PATENT DOCUMENTS 3,161,917 * 12/1964 Wiland .
4,203,219 * 5/1980 Wiener .................................. 433/74
4,300,884 * 11/1981 Camacho .............................. 433/74
4,721,464 * 1/1988 Roden et al. .......................... 433/74
5,129,822 * 7/1992 Dobbs ................................... 433/34
5,647,744 * 7/1997 Squicciarini ........................... 433/34
6,106,284 * 8/2000 Cronin et al. .......................... 433/34

FOREIGN PATENT DOCUMENTS 83 13 606 * 11/1985 (DE) .
38 37 551 * 5/1990 (DE) .
694 293 * 1/1996 (EP) .

OTHER PUBLICATIONS

Deutsches Patentamt, 197 22 989.1–23; Dr. Rainer Hahn, Apr. 3, 1998 International Preliminary Examination Report, PCT/EP98/02601, International Search Report, PCT/EP98/02601, Feb. 5, 1998.

* cited by examiner

Primary Examiner—Ralph A. Lewis

(57) ABSTRACT

The invention relates to a mold for producing the model of a tooth from a dental impression (28), comprising a peripheral wall (12), a model plate (38) which is tightly arranged on the top thereof and an impression spoon (14) bearing the dental impression (28). Said spoon is tightly inserted into the lower end of the peripheral wall (12). The hollow cavity (42) thus obtained is filled with molding material to give a highly precise tooth model requiring no further mechanical processing.

19 Claims, 6 Drawing Sheets

MOLD FOR PRODUCING A MODEL OF A TOOTH

BACKGROUND OF THE INVENTION

1. Field of the Invention

The invention relates to a mould for producing a tooth model from a dental impression.

2. Background Art

Such moulds are known in the form of cup-shaped formed bodies.

To produce a tooth model from a dental impression, the dental impression is filled with a plastic modelling material which hardens. Immediately after filling the dental impression with the modelling material in rare cases, while the modelling material is still soft, a mostly rubber-like mould is applied to the peripheral wall of the dental impression in order, by filling the mould up to a predetermined height, to obtain a base on the tooth model.

To produce artificial teeth, said base is trimmed parallel to the occlusal plane mechanically by grinding; the result is a so-called toothed rim made of modelling material.

Then a drill and a twist drill are used to drill blind holes in the base of the toothed rim, in each case under the teeth to be restored, adjacent teeth or antagonists, and metal pins are introduced and preferably glued into the blind holes.

After subsequent isolation of the base mostly using an alginate-based isolating material, the toothed rim with the glued-in pins is basally aligned and introduced into a mould, which is filled to a height of around two centimeters with preferably the same plastic modelling compound, until the base of the toothed rim is just completely wetted by the plastic modelling compound. Said compound after it has hardened forms the base for the toothed rim; toothed rim and base together form the finished tooth model.

After hardening and mechanical trimming of the base, the toothed rim is sawn in each case at right angles to the tangent predefined by the individual tooth groups right down to the base such that the model teeth to be restored, neighbouring teeth, maxillomandibular segments or any other model teeth or model tooth groups may be individually removed from the base and precisely repositioned by means of the pins.

Such a saw-cut model is a prerequisite for producing any type of artificial tooth from dental impressions.

Another way of producing model bases is such that the parallel-trimmed, conventionally produced toothed rims are provided in a special drilling apparatus with the blind holes for the pins and at the same time mirror-image holes are drilled into a prefabricated base plate made of plastic material for receiving the pins, which are to be glued into the toothed rim, together with the toothed rim. Removal of the prepared teeth is effected by the conventional saw-cut technique. Although this dispenses with the outlay for processing a second plastic modelling compound for producing the base, expensive equipment is necessary.

A particular problem associated with producing tooth models, in particular toothed rims, is the filling of the mostly hydrophobic dental impression with the hydrophilic modelling material, usually dental plaster. The narrow indentations of the individually moulded teeth, undercuts occasioned by the tooth shape and fine delineation of the textured surface of the teeth in most cases promote bubble formation in the tooth model which often makes it necessary to produce a second tooth model. Such a second tooth model however is mostly of an inferior quality to the first tooth model because the removal of the latter from the dental impression simultaneously leads to the breaking-off of fine edges and surface structures as well as fine interdental lamellae or lamellae in the sulcus region.

In addition, defects attributable to the shaping by the dentist to obtain the dental impression are frequently only detectable on the tooth model. Because of the elaborate process of producing the latter, however, defects are mostly not spotted until several days after taking the impression from the patient. In many cases the patient has to be brought back for a new impression to be taken, which entails a high outlay and often leads to poorer impression results because a common consequence of the initial treatment is a tendency to bleed during the follow-up treatment.

SUMMARY OF THE INVENTION

The object of the invention is to provide a mould for producing a tooth model from a dental impression, which enables a simpler processing technique involving only a lower number of working steps and by means of which the number of error sources is reduced and tooth models of greater precision are obtained.

In the mould according to the invention, the bottom wall of the mould is formed by the impression tray used to produce the dental impression, wherein the dental impression for producing the tooth model remains on the impression tray.

The impression tray at least in portions of its outer surface has a precisely predetermined geometry and may without reworking be connected precisely and tightly to the peripheral wall of the mould.

As will become even clearer from the detailed description below, production of a tooth model using the mould according to the invention saves time and costs. In particular, compared to conventional production of the toothed rim, there is no need for mechanical trimming, drilling of the blind holes for the pins or manufacture of the base plate involving repeat processing of modelling material, nor is there any need for expensive equipment for producing the toothed rim.

The use of the mould according to the invention is to a large extent error-tolerant and may be extensively automated.

The invention also makes it possible for the tooth model to be produced directly at the dental surgery. All the dentist need do, after production of the dental impression, is clamp the used impression tray together with the impression itself into the peripheral wall and introduce into the mould thus obtained an adequate amount of modelling material over the dental impression. Only the tooth model thus obtained is then passed on to the dental technician.

Producing the tooth model at the dental surgery also has the advantage that minor defects of the dental impression are easier to spot on the tooth model and the dentist in said case may immediately take another impression from the patient before the latter leaves the premises.

A mould is tightly closed on all sides.

The mould during filling may therefore be acted upon by a pressure below or above atmospheric. The former has the advantage of keeping bubble formation very low. In both cases, the modelling material flows well even into small interstices.

It is moreover possible for a mould prior to introduction of the modelling material, to be thoroughly rinsed with a wetting agent or another treatment medium so that the surface of the impression is optimally prepared for subsequent contact with modelling material.

A mould also easily allows the production of a tooth model which, at its base side, is already flat without machining of the modelling material.

In said case, the development of the invention is advantageous in view of a bubble-free quality of the—during casting—top end face of the tooth model.

The development of the invention also serves to achieve bubble-free, complete filling of the mould with modelling material.

The effect achieved by the development of the invention is that the feeding of modelling material is automatically terminated when the mould is completely full of modelling material.

Sealing connections may be realized in a simple and reliable manner between the peripheral wall and the impression tray and/or the peripheral wall and the model plate.

The development of the invention is advantageous in view of precise, reproducible positioning of a model plate on the peripheral wall.

The development of the invention allows the realization of a tooth model which may then, by means of saw cuts effected transversally relative to the mandibular arch, be made into a saw-cut model in which individual teeth or tooth groups are removable and precisely repositionable.

For said purpose positioning pins may be used, which are embedded in the tooth model and in each case have a positioning portion projecting above the tooth model.

The blind recesses in the model plate may also be made permeable to gas so that the modelling material may penetrate into the blind recesses when the modelling material is introduced under pressure above atmospheric. When it is introduced under pressure below atmospheric, air situated in the blind recesses is extracted. The result is the formation on the tooth model of positioning pegs, which are complementary to the blind recesses.

The development of the invention allows reproducibly precise feeding of the modelling material to the mould cavity.

In said case, the development of the invention guarantees that no air bubbles are trapped between the modelling material and the dental impression.

The development of the invention makes it possible, while using identical basic components, to realize moulds of differing height, thereby also enabling tooth models of differing height to be produced in an identical manner.

The development of the invention in a simple manner allows a tight bracing of the peripheral wall with the model tray and optionally the model plate, particularly also in cases where impression tray as well as optionally model plate and peripheral wall have cooperating positive locking means which ensure, on the one hand, exact alignment of the impression tray in the peripheral wall and, on the other hand, efficient sealing of the mould cavity.

The development of the invention in said case guarantees that, despite the slot provided in the peripheral wall, efficient sealing of the mould cavity is achieved.

The developments of the invention allow external visual checking of the filling of the mould cavity with modelling material, particularly given the use of dyed modelling materials.

The effect achieved by the development of the invention is that the outer surface or outer lateral surface of the tooth model has a shape which is suitable for exact positioning in an articulator or similar apparatus without the outer surface of the tooth model having to be cut for said purpose. Thus, when using a mould according to the invention, there is no longer any troublesome generation of plaster dust or dust from other modelling materials in the dental laboratory.

Embodiments of the invention are described in detail below with reference to the accompanying drawings. Said drawings show:

DETAILED DESCRIPTION OF THE INVENTION

Figure 1:
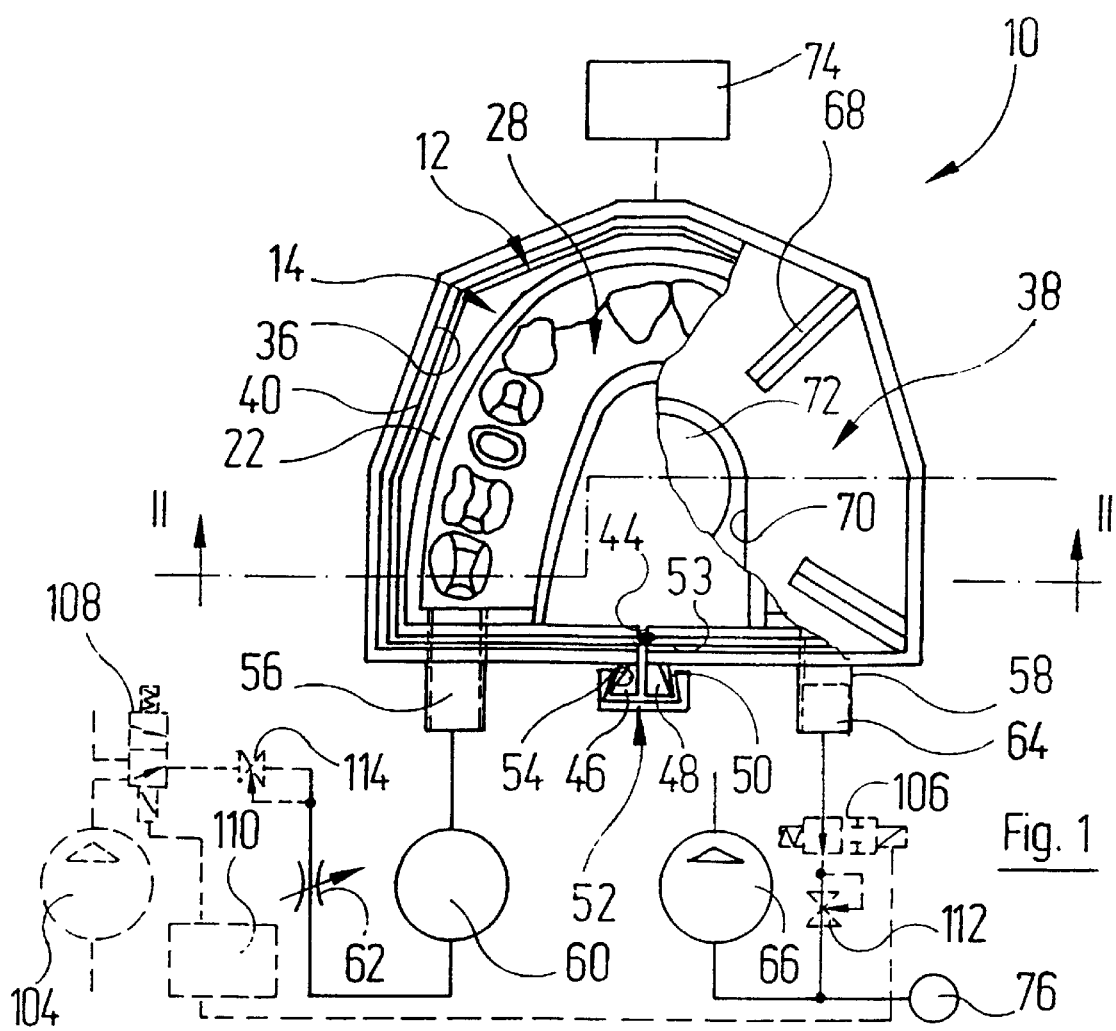
FIG. 1: a plan view of a mould for producing tooth models together with a diagrammatically illustrated device for filling the mould with modelling material, wherein part of a model plate forming the top of the mould is broken away.
Figure 2:
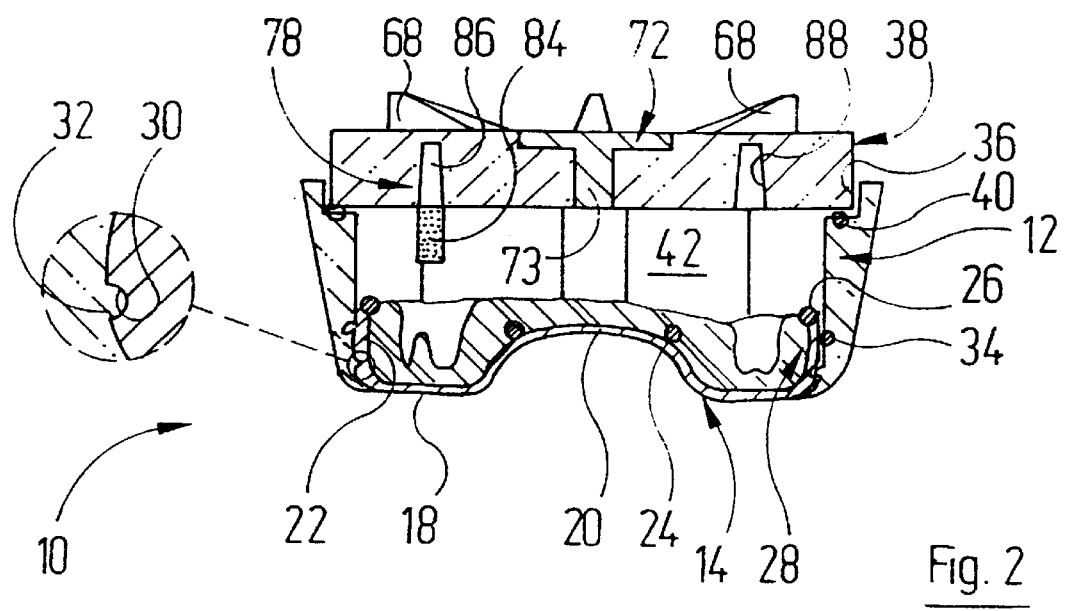
FIG. 2: a transverse section through the mould shown in FIG. 1 along the cranked cutting line II—II of FIG. 1.
Figure 3:
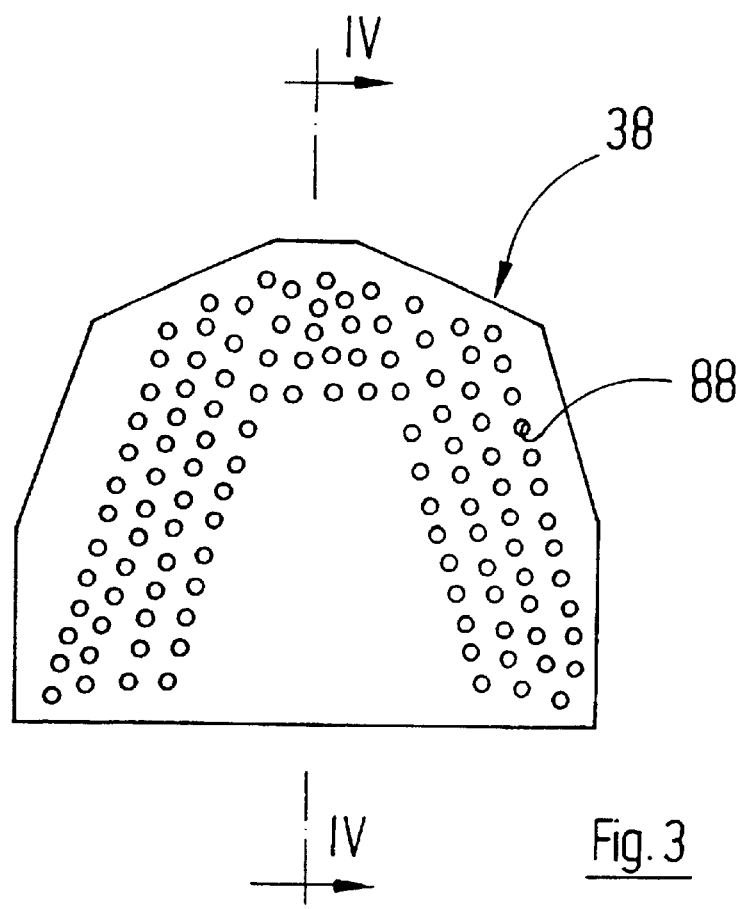
FIG. 3: a plan view of the model-side boundary surface of the model plate of FIGS. 1 and 2.
Figure 4:
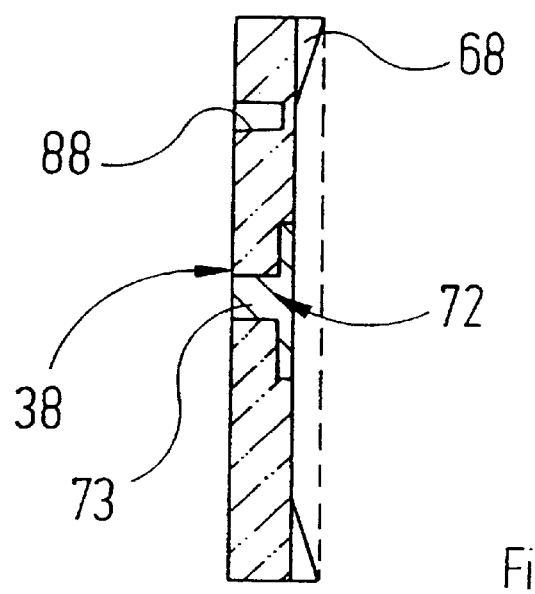
FIG. 4: a longitudinal section through the model plate along the cutting line IV—IV of FIG. 3.

FIGS. 1 and 2 show a mould for producing tooth models, which is denoted as a whole by 10. The mould 10 has a peripheral wall 12, the bottom portion of which is complementary to the outer surface of an impression tray 14.

The illustrated impression tray 14 is a tray for producing supramaxillary impressions and comprises a bottom wall 18, having a middle wall portion 20 modelled on the soft palate, and a boundary wall 22 extending in peripheral direction. Soldered onto the edge of the wall portion 20 and the top end of the boundary wall 22 are wire pieces 24 and 26, which create undercuts, against which a dental impression 28 made e.g. of silicone, alginate or the like is latched.

Provided in the bottom third of the boundary wall 22 is a longitudinally extending groove 30, into which a longitudinally extending rib 32 provided on the inner surface of the peripheral wall 12 positively engages.

A seal 34 is supported via the rib 32 by the peripheral wall 12 and cooperates with the outer surface of the peripheral wall 22. Both by virtue of said seal and also by virtue of the keyed connection between groove 30 and rib 32 an efficient sealing and precise positioning between peripheral wall 12 and impression tray 14 are achieved.

As is clearly evident from FIG. 2, the contour of the inner surface of the peripheral wall 12 corresponds to the contour of the outer surface of the boundary wall 22, which likewise assists sealing and good positioning. The outer surface of the peripheral wall 12 moreover verges smoothly into the outer surface of the impression tray 14.

The outer surface of the peripheral wall 12 extends with an obliquely outward slope so that the thickness of the peripheral wall 12 increases in an upward direction.

A marginal recess 36 extending in longitudinal direction of the peripheral wall 12 is set back from the top end face of the peripheral wall 12. A bottom portion of a model plate 38 engages positively into the marginal recess 36. Inserted into the bottom of the marginal recess 36 is a seal 40, which cooperates with the edge of the, in FIG. 2, bottom boundary surface of the model plate 38.

The peripheral wall 12, the impression tray 14, the dental impression 28 carried by the latter and the model plate 38 therefore together delimit an outwardly sealed mould cavity 42.

To enable fitting of the peripheral wall 12 on the impression tray 14, the, in FIG. 1, bottom wall portion of the peripheral wall 12 is provided with a slot 44. The peripheral wall 12 is made of a substantially rigid yet slightly elastically deformable plastic material so that the peripheral wall 12 by virtue of the elastic expansion enabled by the slot 44 may be clipped onto or removed from the impression tray 14.

The, in FIG. 1, bottom wall portion of the peripheral wall 12 has in the vicinity of the slot 44 two dovetail parts 46, 48, the dovetail faces 50 of which widen in a downward direction. When a clamping part 52 provided with complementary inner dovetail faces 54 is slipped onto the dovetail faces 50, the peripheral wall 12 is drawn together at the slot 44 and hence applied tightly and sealingly against the outer surface of the impression tray 14. At the same time, a seal 53 lying between the lateral faces of the slot 44 is placed under initial tension.

Two connection pieces 56, 58 are provided in the outer-lying regions of the bottom wall portion of the peripheral wall 12. of said connection pieces the left is tightly connected to the outlet of a reservoir 60 containing a liquid modelling material (e.g. plaster). A ventilation connection of the reservoir 60 is connected by an adjustable throttle 62 to the environment.

The connection piece 58 contains a stopper 64, which is permeable to gas but acts as an obstruction to modelling material. The connection piece 58 is connected by the stopper 64 to the suction opening of a suction pump 66. The outlet of the latter is connected likewise to the ambient atmosphere.

Figure 6:
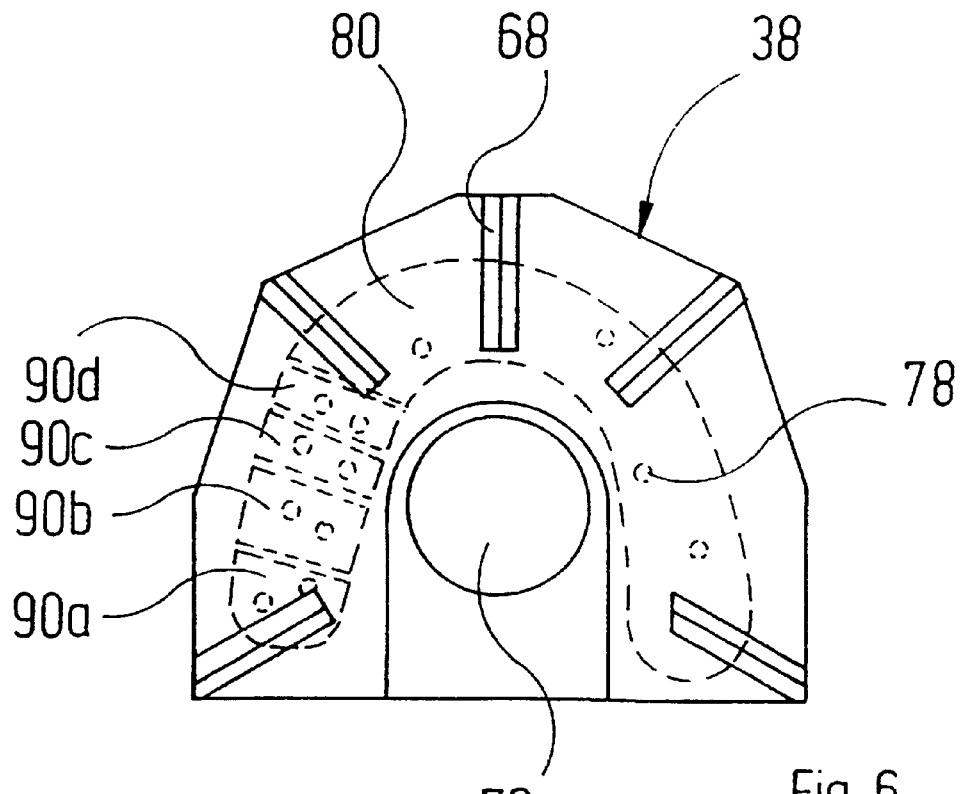
FIG. 6: a plan view of the holder-side boundary surface of the model plate shown in FIG. 5.

As is clearly evident from FIGS. 1, 2 and 6, the boundary surface of the model plate 38 remote from the mould cavity 42 carries radial positioning ribs 68, which have a substantially triangular basic cross section and slope down towards the middle of the model plate 38. The positioning ribs 68 cooperate with complementary positioning grooves of a non-illustrated holding part, as is customary with divided magnetic base systems. The holding part in turn is clamped into the articulator or a machining apparatus of the dental technician.

The outer-lying side of the model plate 38 moreover carries inside a flat indentation 70, which is open towards the edge, a disk-shaped fixing part 72, which has a shaft 73 made of magnetic or magnetizable material embedded in the model plate and cooperates with a counterpart fixing part, which is carried by the holding part and likewise made of magnetic or magnetizable material. In said manner the model plate 38 is releasably fixed on the holding part.

The procedure for producing a tooth model using the mould described above is as follows:

The impression tray 14 carrying the dental impression 28 is latched into the peripheral wall 12 and the model plate 38 is inserted into the top end of the peripheral wall 12. Then the clamping part 52 is slipped onto the dovetail parts 46, 48 so that the above-mentioned parts are braced with one another.

The suction pump 66 is then set in operation and the mould cavity 42 is filled with liquid modelling material at a rate predetermined by the adjustment of the throttle 62. Alternatively, the modelling material may be fed in under pressure above atmospheric, as will be described in greater detail further below with reference to FIG. 11.

Preferentially, the mould cavity 42 is first evacuated and then the modelling material is fed in under pressure above atmospheric. A compressor 104 and a ⅔-way and a ⅗-way magnetic valve 106 and 108 respectively, which are operated by a suitable control unit 110, are used for said purpose. Pressure regulators 112 and 114 are used to preselect the pressure below and above atmospheric in the mould cavity 42. Said variant is shown by dashes in FIG. 1.

The filling operation may be visually checked through the model plate 38 and/or the peripheral wall 12. Additional shaking or vibrating of the mould 10 may even out the filling operation and cause any air bubbles trapped under modelling material in the indentations of the dental impression 28 to rise. This is preferably effected by means of a mechanical vibrator 74, which is mechanically coupled to the mould 10 in the manner indicated by dashes in FIG. 1.

At the end of the filling operation the liquid modelling material then reaches the stopper 64. As the modelling material is unable to penetrate the stopper, the suction pump 66 then operates against a closed volume, which is acoustically easily perceptible. Where desired, it is also possible to connect to the line extending between the stopper 64 and the suction pump 66 a pressure monitor 76, the output signal of which may be used to sound an alarm.

Once the modelling material has hardened, the clamping part 52 is slipped down off the dovetail parts 46, 48. The model plate 38 may then be lifted in an upward direction from the impression tray 14 and the dental impression 28 carried by the latter.

Figure 5:
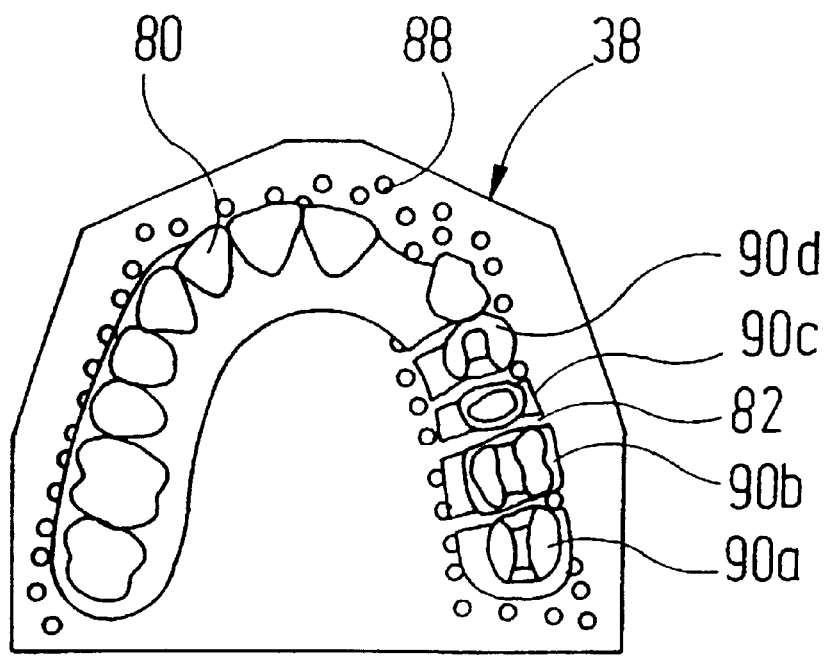
FIG. 5: a plan view of the model-side boundary surface of the model plate with a sawn toothed rim of a mandibular arch carried by the model plate.

When, prior to filling the mould cavity 42, positioning pins 78 have been inserted in the model plate 38 at points where the finished tooth model 80 is later to have removable segments or positioning pins, it is possible in the manner shown in FIG. 5 then to produce said segments by means of saw cuts 82 so that the corresponding maxillomandibular segments are individually removable from the model plate 38 and subsequently also precisely repositionable there.

The positioning pins 78 each have an anchoring portion 84, which is integrally cast in the modelling material and for the purpose of improving the frictional engagement is provided with a knurl comprising grooves or the like. The positioning pins 78 moreover have truncated cone-shaped positioning portions 86, which are complementary to blind recesses 88 provided in a grid arrangement on the boundary surface of the model plate 38 directed towards the mould cavity. FIG. 5 shows four different removable segments 90a, 90b, 90c and 90d of the tooth model 80, which correspond to two cavities set back from the occlusal surface, one truncated cone-like crown preparation and one lateral cavity of a tooth.

In the embodiments described below, mould parts which have already been described above with reference to FIGS. 1 to 6 are once more provided with the same reference characters. Said mould parts are also not described in detail again below.

Figure 7:
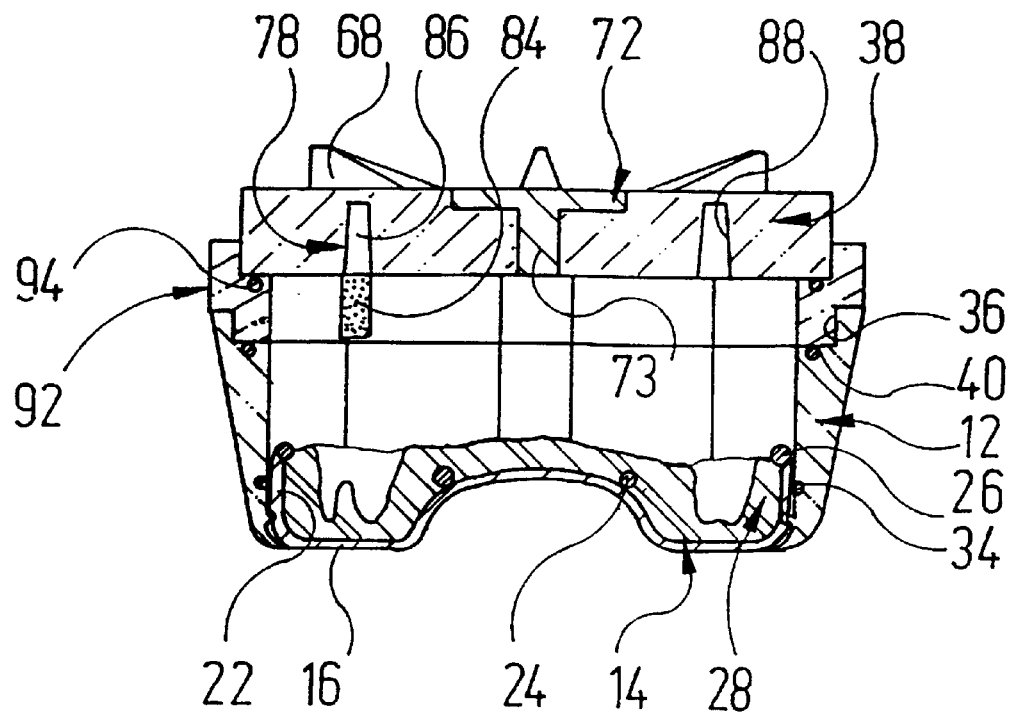
FIG. 7: a section similar to FIG. 2 through a modified mould used to produce higher tooth models.

In the modified mould 10 shown in FIG. 7, a higher mould cavity 42 is achieved by inserting between the top end of the peripheral wall 12 and the model plate 38 a distance element 92, the inside and outside edge contour of which corresponds to the inside and outside edge contour of the top end of the peripheral wall 12. The bottom end face of the distance element 92 is complementary to the top end face of the peripheral wall 12, and the top end face of the distance element 92 has the same geometry as the top end face of the peripheral wall 12.

A further seal 94 ensures sealing between the distance element 92 and the model plate 38. It goes without saying that the dentist or dental technician will stock a plurality of distance elements 92 so that the height of the mould cavity 42 may be selected as close as possible to required height of the tooth model. To adjust even larger mould cavities 42, a plurality of such distance elements may also be stacked one on top of the other.

Figure 8:
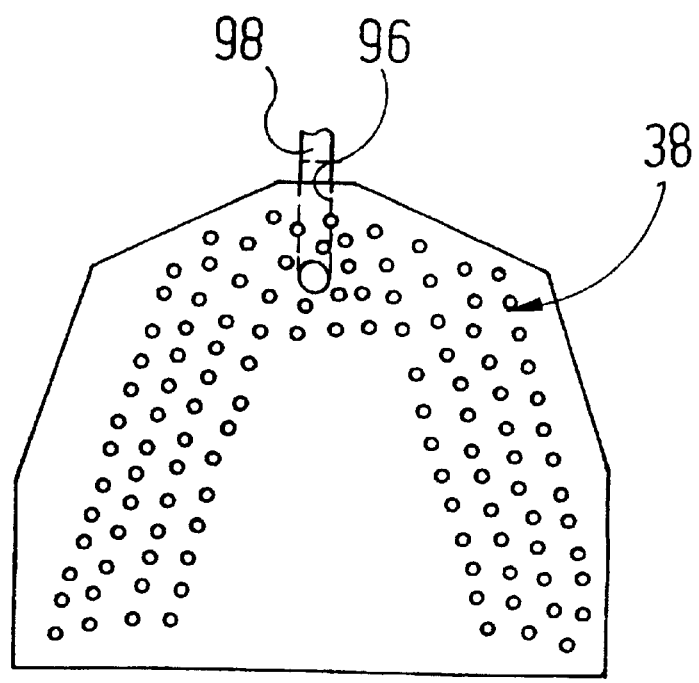
FIG. 8: a view similar to FIG. 3, which shows a modified model plate.

FIG. 8 shows a modified model plate 38, which is provided with a channel 96. Said channel is connected by a stopper 98, which has the same properties as the stopper 64, to the suction side of the suction pump 66.

In a further modification, the model plate 38 may also be provided with a plurality of such channels 96, which are provided [sic] in each case by an associated stopper 98 to the suction pump 66.

When a model plate 38 has such channels 96, it is also possible to dispense with the connection piece 58.

Figure 9:
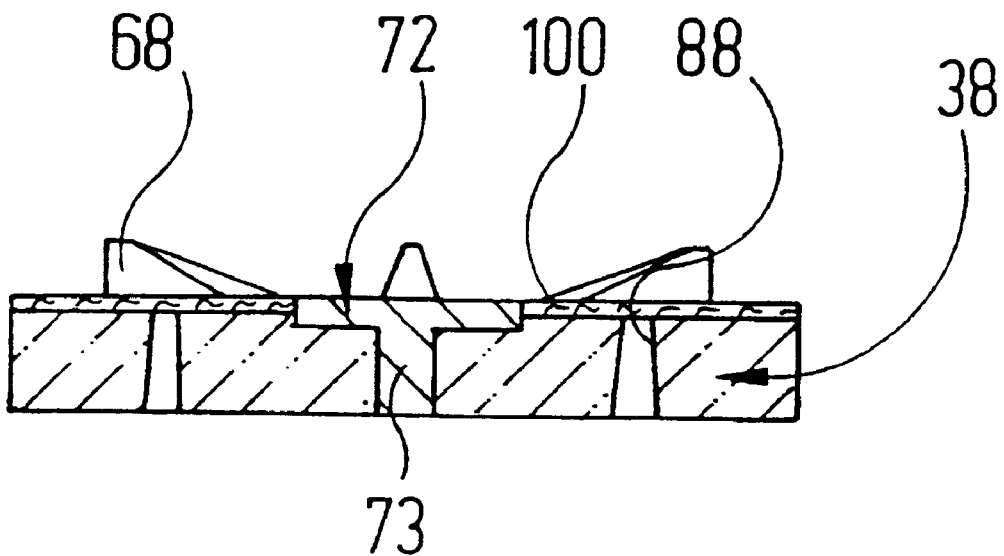
FIGS. 9 and 10: sections through further modified model plates, which are similar to the section of FIG. 2.
Figure 10:
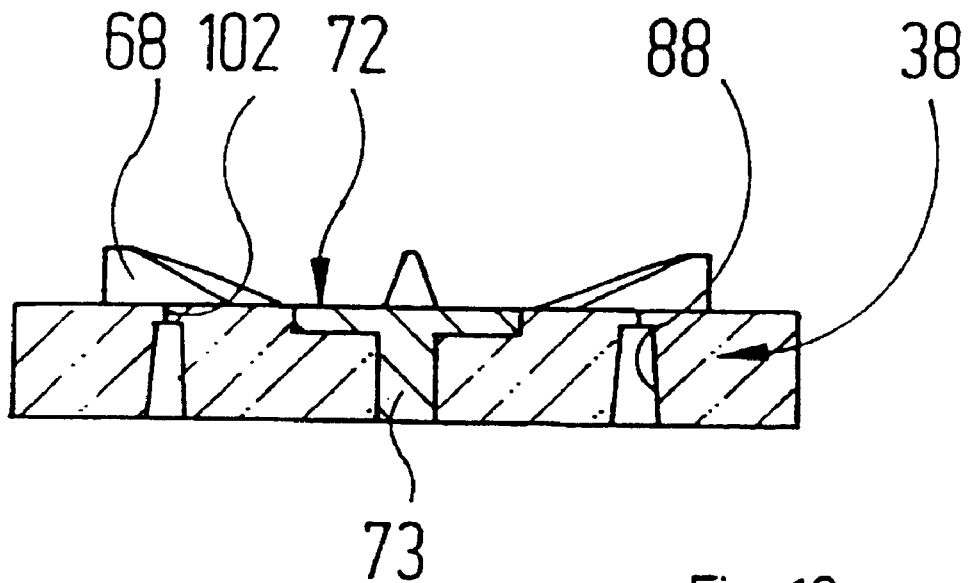

In the further modified model plate according to FIG. 9, the bases of the blind recesses 88 are formed by a material layer 100, which is permeable to gas but impermeable to modelling material.

When a material layer 100 which is permeable to gas in one direction only but blocks in the other direction (e.g. a semi-permeable membrane) is used, it is then also possible to evacuate the mould cavity of such a modified mould.

Instead of this, according to claim 10 very thin ventilation bores 102 extending from the bases of the blind recesses 88 to the outer-lying side of the model plate 38 may be provided.

When, instead of such a model plate-gripping mould 10 being operated with pressure below atmospheric, the modelling material is fed to the mould under pressure above atmospheric, air may escape from the blind recesses 88 and modelling material may penetrate into the blind recesses 88. The result in said case is a plurality of positioning pegs formed on the tooth model 80. Thus, no positioning pins are required.

When the mould 10 is acted upon by pressure above atmospheric, removable tooth model segments may also be subsequently defined simply by sawing through the tooth model at the required points. In an embodiment according to FIGS. 1 to 6, however, before introducing the modelling material the points at which removable model segments are to be situated have to be fixed by suitably equipping the model plate 38 with positioning pins 78.

Figure 11:
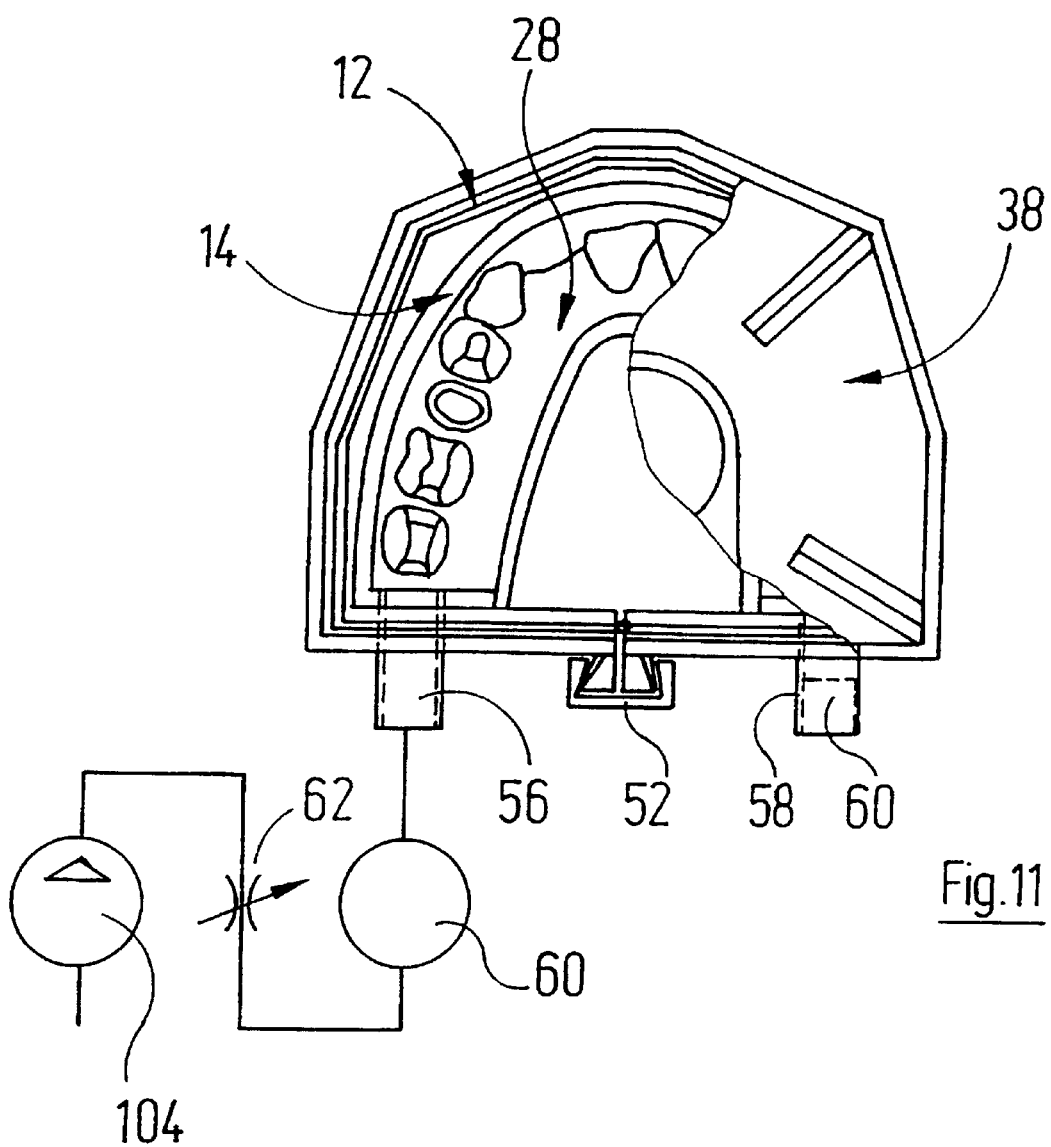
FIG. 11: a view similar to FIG. 1 but showing a modified device for filling the mould with modelling material.

The acting upon the mould cavity 42 with pressure above atmospheric during introduction of the modelling material is achieved according to FIG. 11 by connecting the inlet of the throttle 62 to the outlet of a compressor 104. The stopper 64 is then flow-connected directly to the ambient atmosphere.

Alternatively, a syringe or a mechanical feed pump may be used for feeding in the modelling material under a pressure above atmospheric.

To prevent the model plate 38 from lifting off the peripheral wall 12 when a pressure above atmospheric is admitted into the mould cavity 42, a keyed connection between model plate 38 and peripheral wall 12 may be provided, e.g. a groove, which corresponds to the groove 30, in the outer surface of the assembly plate 38 and a rib, which corresponds to the rib 32, carried by the side wall of the marginal recess 36.

In practice, work is carried out with a small number of differently dimensioned impression trays 14 in order to cover differently sized jaws of patients. It goes without saying that the dentist or dental technician will stock a corresponding number of differently sized peripheral walls 12 and model plates 38 so that with the various impression tray sizes tooth models may be produced in the manner described above.

It goes without saying that prior to the feeding of the modelling material the surfaces delimiting the mould cavity 42 are coated with a suitable release agent (e.g. release agent spray) so that the tooth model after hardening easily detaches from said surfaces.

What is claimed is:

1. Mould for producing a tooth model from a dental impression, having a bottom mould, which receives the dental impression (28) and comprises a peripheral wall (12) and a bottom wall, wherein the peripheral wall (12) is sealingly connected to an impression tray (14), which forms the bottom wall and carries the dental impression (28), and a model plate (38) is mountable sealingly onto the top end of the peripheral wall (12), characterized in that the peripheral wall (12) and the model plate (38) together have at least two liquid openings (56, 58, 96), which communicate with the mould cavity (42) delimited by the peripheral wall (12), the impression tray (14) and the model plate (38).

2. Mould according to claim 1, characterized in that the liquid openings (56, 58, 96) of the mould-side boundary surface of the model plate (38) are adjacent.

3. Mould according to claim 1, characterized in that the liquid openings (56, 58, 96) are connected to portions of the mould cavity (42) which, in terms of flow, lie opposite one another.

4. Mould according to claim 1, characterized in that at least one of the liquid openings (56, 58, 96) has a stopper (64, 98), which is permeable to gas but not to modelling material.

5. Mould according to claim 1, characterized in that the sealing connection between the peripheral wall (12) and the impression tray (14) comprises cooperating positive locking means (30, 32), which are provided at the inside of the peripheral wall (12) and the outside of the impression tray (14) respectively.

6. Mould according to claim 1, characterized in that the sealing connection between the peripheral wall (12) and the impression tray (14) comprises mutually complementary surface portions of the inner surface of the peripheral wall (12) and of the outer surface of the impression tray (14).

7. Mould according to claim 1, characterized in that the sealing connection between the peripheral wall (12) and the impression tray (14) comprises at least one sealing element (34).

8. Mould according to claim 1, characterized in that the model plate (38) engages positively into a recess (36), which is provided in the top end face of the peripheral wall (12).

9. Mould according to claim 1, characterized in that the model plate (38) is provided with a plurality of undercut-free blind recesses (88) arranged in a grid, wherein the latter preferably taper towards the blind recess base.

10. Mould according to claim 9, characterized by positioning pins (78), which comprise a positioning portion (86) complementary to the blind recesses (88) and an anchoring portion (84) firmly embeddable in the modelling material.

11. Mould according to claim 9, characterized in that a top portion of the blind recesses, preferably the base of the blind recesses, is permeable to gases but not to modelling material.

12. Mould according to one of claim 1, characterized in that at least one of the liquid openings (56, 58, 96) is connected to a source (60) of modelling material.

13. Mould according to claim 1, characterized by a device (66; 104) for generating a pressure difference between at least two of the liquid openings (56, 58, 96).

14. Mould according to claim 1, characterized by a lengthening part (92) for the peripheral wall (12) having a bottom end face complementary to the top end face of the peripheral wall and a top end face corresponding to the peripheral wall (12).

15. Mould according to claim 1, characterized in that the peripheral wall (12) has a slot (44) interrupting it in peripheral direction, and that a clamping device (46 to 50) is associated with the slot (44).

16. Mould according to claim 15, characterized in that a sealing device (53) is associated with the slot (44).

17. Mould according to claim 1, characterized in that the peripheral wall (12) is made of transparent or translucent material.

18. Mould according to claim 1, characterized in that the model plate (38) is made of transparent or translucent material.

19. Mould according to claim 1, characterized in that the inner surface of the top portion of the peripheral wall (12) has the shape of a polygon.

\* \* \* \* \*